US00PP16842P2

(12) United States Plant Patent
Koppe

(10) Patent No.: US PP16,842 P2
(45) Date of Patent: Jul. 18, 2006

(54) ***BEGONIA* PLANT NAMED 'BETULIA BRIGHT PINK'**

(50) Latin Name: *Begonia×hybrida*
Varietal Denomination: Betulia Bright Pink

(75) Inventor: Lubbertus H. Koppe, Ermelo (NL)

(73) Assignee: Koppe Royalty B.V., Ermelo (NL)

( * ) Notice: Subject to any disclaimer, the term of this patent is extended or adjusted under 35 U.S.C. 154(b) by 0 days.

(21) Appl. No.: 11/119,065

(22) Filed: Apr. 30, 2005

(51) Int. Cl.
*A01H 5/00* (2006.01)

(52) U.S. Cl. ..... Plt./348
(58) Field of Classification Search ..... Plt./348
See application file for complete search history.

(56) References Cited

PUBLICATIONS

UPOV Plant Variety Database 2005/04 search for 'Betulia Bright Pink'.*

* cited by examiner

*Primary Examiner*—Kent Bell
*Assistant Examiner*—Annette H Para
(74) *Attorney, Agent, or Firm*—C. A. Whealy

(57) ABSTRACT

A new and distinct cultivar of *Begonia* plant named 'Betulia Bright Pink', characterized by its upright and mounded plant habit; single to semi-double flowers that are bright red purple in color and held above the foliage; and excellent postproduction longevity.

1 Drawing Sheet

Botanical designation: *Begonia×hybrida.*
Cultivar denomination: 'Betulia Bright Pink'.

BACKGROUND OF THE INVENTION

The present Invention relates to a new and distinct cultivar of *Begonia* plant, botanically known as *Begonia× hiemalis,* commercially known as Elatior *Begonia,* and hereinafter referred to by the name 'Betulia Bright Pink'.

The new *Begonia* was discovered by the Inventor in a controlled environment in Ermelo, The Netherlands, in May, 2001, as a naturally-occurring whole plant mutation of *Begonia×hiemalis* 'Betulia Pink', disclosed in U.S. Plant Pat. No. 12,598. The new *Begonia* was observed as a single plant in a group of flowering plants of the parent cultivar. The selection of this plant was based on its unique flower coloration.

Asexual reproduction of the new *Begonia* by cuttings in a controlled environment in Ermelo, The Netherlands, has shown that the unique features of this new *Begonia* are stable and reproduced true to type in successive generations.

SUMMARY OF THE INVENTION

The cultivar 'Betulia Bright Pink' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Betulia Bright Pink'. These characteristics in combination distinguish 'Betulia Bright Pink' as a new and distinct *Begonia:*

1. Upright, compact and mounded plant habit.
2. Single to semi-double flowers that are bright red purple in color and held above the foliage.
3. Excellent postproduction longevity.

Plants of the new cultivar are most similar to plants of the parent, the cultivar Betulia Pink. Plants of the new cultivar differ from plants of the cultivar Betulia Pink primarily in flower color.

BRIEF DESCRIPTION OF THE PHOTOGRAPHS

The accompanying colored photographs illustrate the overall appearance of the new *Begonia,* showing the colors as true as it is reasonably possible to obtain in colored reproductions of this type. Colors in the photographs may differ slightly from the color values cited in the detailed botanical description which accurately describe the colors of the new *Begonia.*

The photograph at the top of the sheet comprises a side perspective view of a typical flowering plant of 'Betulia Bright Pink'.

The photograph at the center of the sheet is a close-up view of the upper surfaces of developing and fully expanded flowers and leaves of 'Betulia Bright Pink'.

The photograph at the bottom of the sheet is a close-up view of the lower surfaces of developing and fully expanded flowers and leaves of 'Betulia Bright Pink'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Ermelo, The Netherlands, under commercial practice in a glass-covered greenhouse. Average day and night temperatures were about 20° C. during the first three to four weeks then lowered to an average day and night temperature of 19° C. until flowering. Four weeks after planting rooted cuttings in 12-cm containers, one week of long nyctoperiods of 16 hours was given followed by short nyctoperiods of eight hours until flowering. Plants used for the photographs and the description were about four months old. Measurements and numerical values represent averages for typical flowering plants.

Botanical classification: *Begonia×hiemalis* cultivar Betulia Bright Pink.

Commercial classification: Elatior *Begonia*.

Parentage: Naturally-occurring whole plant mutation of *Begonia×hiemalis* cultivar Betulia Pink, disclosed in U.S. Plant Pat. No. 12,598.

Propagation:

*Type.*—Cuttings.

*Time to develop roots.*—About 40 days at temperatures of 20 to 22° C.

*Root description.*—Fine, fibrous, well-branched and spreading. Plants of the new *Begonia* have not been observed to form tubers.

Plant description:

*Plant form.*—Upright, compact and mounded plant habit, inverted triangle; freely branching with good stem and stem base strength. Flowers are single to semi-double and abundant. Plants flower continuously.

*Growth habit.*—Moderate growth rate, vigorous growth habit. Suitable for 11 to 15-cm containers. Under optimal conditions, usually about four months are required to produce proportional 13-cm potted plants from cuttings. Vegetative shoots are formed at basal nodes and flowering shoots are formed at upper nodes.

*Plant height.*—About 20 to 25 cm.

*Plant width.*—About 35 cm.

*Leaves.*—Arrangement: Simple, alternate. Developing leaves, length: About 3.5 to 6 cm. Developing leaves, width: About 4.5 to 7 cm. Fully expanded leaves, length: About 9 to 12 cm. Fully expanded leaves, width: About 8 to 10 cm. Shape: Asymmetrical, more or less reniform. Apex: Acuminate. Base: Cordate. Margin: Doubly serrate. Texture, upper and lower surfaces: Glabrous, smooth. Venation pattern: Palmate. Color: Developing leaves, upper surface: 137A. Developing leaves, lower surface: 191A to 191B. Fully expanded leaves, upper surface: 147A. Fully expanded leaves, lower surface: 191A to 191B. Venation, upper and lower surfaces: 144A. Petiole length: About 1 to 7.5 cm. Petiole texture, upper and lower surfaces: Pubescent. Petiole color, upper and lower surfaces: 184B.

Flower description:

*Flowering habit.*—Single to semi-double flowers with numerous tepals arranged in axillary cymes. Usually four to seven flowers per cyme. Many cymes in flower simultaneously. Flowers positioned above the foliage. Flowering continuous.

*Natural flowering season.*—Plants will flower year around regardless of nyctoperiod, however plants flower earlier and more abundantly from mid-February until November in the Northern Hemisphere.

*Flowers.*—Shape: Rounded. Diameter: About 4 to 5.5 cm. Depth (height): About 2 cm.

*Flower buds.*—Length: About 1 to 1.8 cm. Diameter: About 1 to 1.5 cm. Color: 53B.

*Tepals.*—Arrangement: Rosette. Shape: Rounded flabellate. Apex: Rounded. Margin, outer and inner tepals: Slightly crenate. Quantity per flower: Usually about four to eight per flower. Size: Outer tepals: Length: About 2.8 to 3 cm. Width: About 2.4 to 2.6 cm. Inner tepals: Length: About 1.6 to 2.3 cm. Width: About 1.4 to 2.3 cm. Texture, upper and lower surfaces: Smooth, glabrous; glabrous. Color: When opening, outer and inner tepals, upper and lower surfaces: 57A. Fully opened, outer and inner tepals, upper surface: 61C; flower color does not fade with subsequent development. Fully opened, outer and inner tepals, lower surface: 54A to 54B.

*Flower bracts.*—Arrangement: Two, opposite. Shape: Broadly cordate. Apex: Rounded. Margin: Serrate. Texture, upper and lower surfaces: Smooth, glabrous. Color, upper and lower surfaces: 139D blushed with close to 59A.

*Peduncles.*—Angle: Erect. Length: About 4 to 6 cm. Texture: Smooth, glabrous. Color: 166D.

*Pedicels.*—Angle: Erect. Length: About 5 to 25 mm. Texture: Pubescent. Color: 180A.

*Reproductive organs.*—Stamens: None observed. Pistils: None observed.

*Seed.*—Seed production has not been observed as reproductive organs are not formed.

Postproduction longevity: Individual flowers: Generally about 2 to 3 weeks. Whole plants: About 6 weeks under interior conditions.

Disease/pest resistance: Resistance to pathogens and pests common to *Begonia* has not been observed.

It is claimed:

1. A new and distinct cultivar of *Begonia* plant named 'Betulia Bright Pink', as illustrated and described.

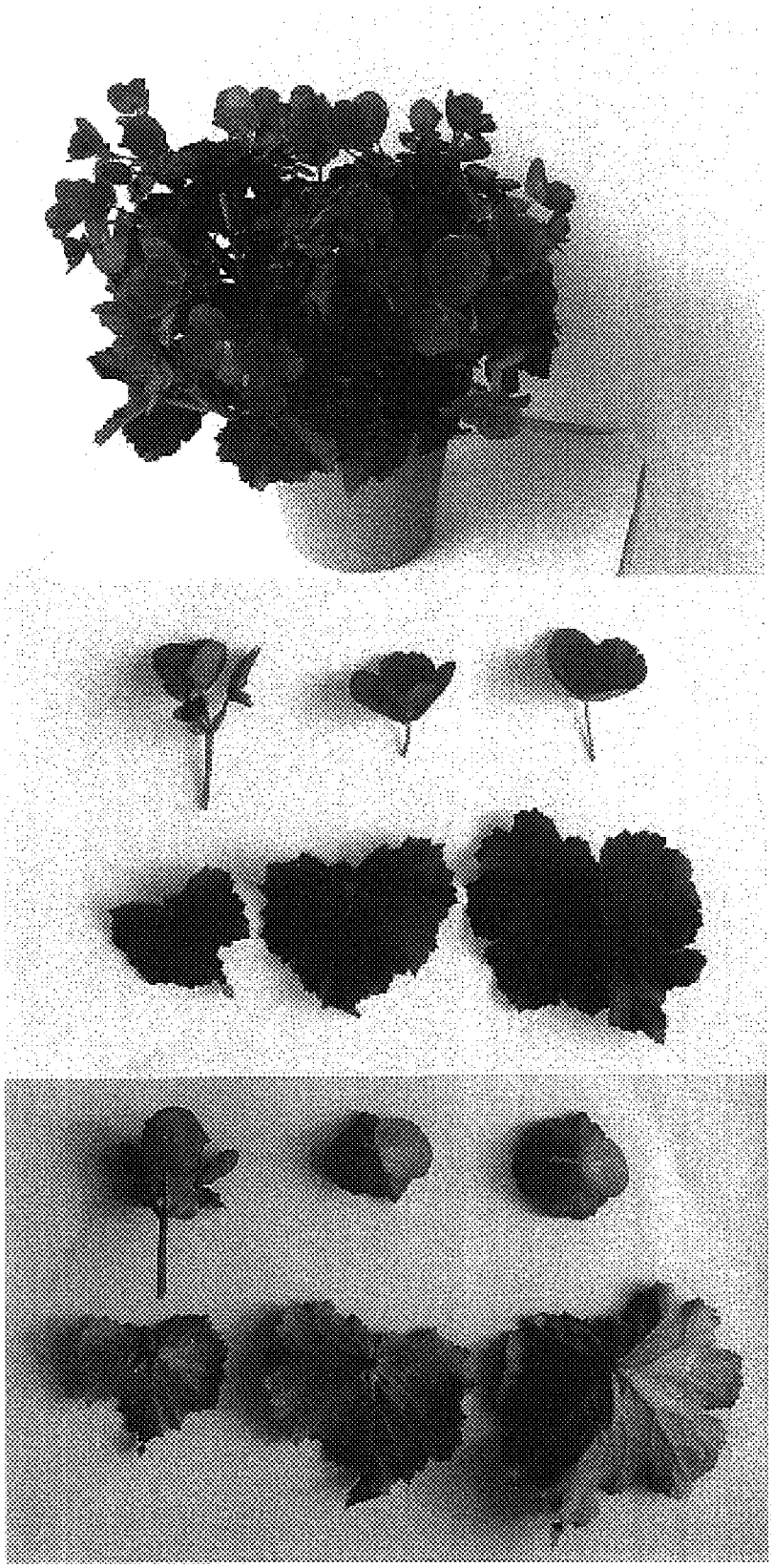

* * * * *